United States Patent
Peters et al.

(10) Patent No.: US 6,815,438 B2
(45) Date of Patent: Nov. 9, 2004

(54) HETEROARYL-DIAZABICYCLOALKANES

(75) Inventors: Dan Peters, Malmo (SE); Gunnar M. Olsen, Frederiksberg (DK); Elsebet Ostergaard Nielsen, Kobenhavn K. (DK); Philip K. Ahring, Bagsvaerd (DK); Simon Feldbaek Nielsen, Herlev (DK); Tino Dyhring Jorgensen, Solrod Strand (DK)

(73) Assignee: Neurosearch A/S, Ballerup (DK)

( * ) Notice: Subject to any disclaimer, the term of this patent is extended or adjusted under 35 U.S.C. 154(b) by 78 days.

(21) Appl. No.: 10/130,099

(22) PCT Filed: Dec. 14, 2000

(86) PCT No.: PCT/DK00/00696

§ 371 (c)(1),
(2), (4) Date: May 14, 2002

(87) PCT Pub. No.: WO01/44243

PCT Pub. Date: Jun. 21, 2001

(65) Prior Publication Data

US 2003/0004153 A1 Jan. 2, 2003

(30) Foreign Application Priority Data

Dec. 14, 1999 (DK) .......................................... 1999 01790

(51) Int. Cl.$^7$ ........................ A61K 31/33; A61K 31/46; C07D 401/00; C07D 471/00
(52) U.S. Cl. ........................ 514/183; 514/185; 514/279; 514/300; 514/334; 546/113; 546/196; 546/199
(58) Field of Search ................................. 514/183, 185, 514/279, 300, 334, 311, 312, 313, 316; 546/113, 196, 199, 26, 112, 134, 135, 137, 152, 187, 159

(56) References Cited

U.S. PATENT DOCUMENTS

| 4,451,473 A | 5/1984 | Nador et al. |
| 5,071,999 A | 12/1991 | Schenke et al. |
| 5,468,742 A | 11/1995 | Petersen et al. |
| 5,659,038 A | 8/1997 | Himmler et al. |

FOREIGN PATENT DOCUMENTS

| EP | 0 470 578 A | 2/1992 |
| EP | 0 153 163 A | 8/1995 |
| EP | 0 787 720 A1 | 8/1997 |
| JP | 63 281158 A | 11/1988 |
| JP | 63281158 | * 11/1988 |
| JP | 09 255679 A | 9/1997 |
| JP | 09255679 | * 5/1999 |
| WO | 96 07656 A | 3/1996 |
| WO | 96 12704 A | 5/1996 |
| WO | 96 39407 A | 12/1996 |
| WO | 97 11945 A | 4/1997 |
| WO | 98 54182 A | 12/1998 |
| WO | 99 21834 A | 5/1999 |
| WO | 99 31100 A | 6/1999 |
| WO | 00 44755 A | 8/2000 |
| WO | 00 55143 A | 9/2000 |
| WO | 00 66586 A | 11/2000 |

OTHER PUBLICATIONS

Chemical Abstract DN 111:15252, also cited as JP 63281158.*
Chemical Abstract DN 111:15252, also cited as JP 63281158.*
Cecil's Textbook of Medicine, vol. 2, 20$^{th}$ Edition, pp. 1992–1996(1996).*
Coyle et al, Science, 219, 1184–1190(1983).*
Lingford–Huges et al, PubMed Abstract 12697627, also cited as Br. med.Bull. 65,209–22(2003).*
PubMed Abstract 12774304, also cited as Synapse, 49/3, 195–205(2003).*
PubMed Abstract12076999, also cited asBrain. 125/7, 1484–95(2002).*
Ohnmacht, Cyrus et al., J. Heterocycl Chem., vol. 20, No. 2, pp. 321–329 (1983).

* cited by examiner

Primary Examiner—Richard L. Raymond
Assistant Examiner—Sudhaker B. Patel
(74) Attorney, Agent, or Firm—Birch, Stewart, Kolasch & Birch, LLP

(57) ABSTRACT

The present invention relates to novel heteroaryl-diazabicycloalkanes which are found to be cholinergic ligands at the nicotinic Acetyl Choline Receptors. Due to their pharmacological profile the compounds of the invention may be useful for the treatment of diseases or disorders as diverse as those related to the cholinergic system of the central nervous system (CNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

6 Claims, No Drawings

HETEROARYL-DIAZABICYCLOALKANES

This application is the national phase under 35 U.S.C. §371 of PCT International Application No. PCT/DK00/00696 which has an International filing date of Dec. 14, 2000, which designated the United States of America.

TECHNICAL FIELD

The present invention relates to novel heteroaryl diazabicycloalkanes, which are found to be cholinergic ligands at the nicotinic Acetyl Choline Receptors.

Due to their pharmacological profile the compounds of the invention may be useful for the treatment of diseases or disorders as diverse as those related to the cholinergic system of the central nervous system (CNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic ACh receptors dominate quantitatively over nicotinic ACh receptors in the brain area important to memory and cognition, and much research aimed at the development of agents for the treatment of memory related disorders have focused on the synthesis of muscarinic ACh receptor modulators.

Recently, however, an interest in the development of nicotinic ACh receptor modulators has emerged. Several diseases are associated with degeneration of the cholinergic system, i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

SUMMARY OF THE INVENTION

The present invention is devoted to the provision novel nicotinic receptor modulators, which modulators are useful for the treatment of diseases or disorders related to the cholinergic receptors, and in particular the nicotinic ACh receptor (nAChR).

Due to their pharmacological profile the compounds of the invention may be useful for the treatment of diseases or disorders as diverse as those related to the cholinergic system of the central nervous system (CNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides a diazabicycloalkane derivative of Formula I

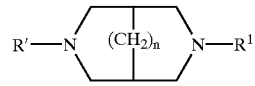

in labelled or unlabelled form, or any of its enantiomers or any mixture of enantiomers, or a pharmaceutically acceptable salt thereof or a prodrug thereof;

wherein n represents 0, 1 or 2;

R' represents hydrogen, an alkyl group, an aryl group, an aralkyl group or a fluorescent group; and $R^1$ represents a mono- or poly-heterocyclic group, which heterocyclic group may be substituted one or more times with substituents selected from the group consisting of alkyl, cycloalkyl, cycloalkylalkyl, alkenyl, alkynyl, methylenedioxy, hydroxy, alkoxy, alkoxy-alkyl, alkoxy-alkoxy, aryloxy, sulfhydryl, thioalkoxy, alkylcarbonyloxy, halogen, $CF_3$, $OCF_3$, CN, and nitro;

or which heterocyclic group may be substituted once with another mono- or poly-heterocyclic group, a mono- or polycyclic aryl group, or a mono- or polycyclic aralkyl group;

and/or which heterocyclic group may be substituted with one or more fluorescent groups.

In another aspect the invention provides a pharmaceutical composition comprising a therapeutically effective amount of the diazabicycloalkane derivative of the invention, or a pharmaceutically acceptable addition salt thereof, together with at least one pharmaceutically acceptable carrier or diluent.

In a third aspect the invention provides an assay kit comprising the pharmaceutical composition of the invention in a unit dosage form in a suitable container.

In a fourth aspect the invention relates to the use of the diazabicycloalkane derivative of the invention for the manufacture of a medicament for the treatment or alleviation of a disease or disorder of a living animal body, including a human, which disease or disorder is responsive to the action of a nicotinic Acetyl Choline Receptor (nAChR) modulator.

In a fifth aspect the invention provides a method of the treatment or alleviation of a disease or disorder of a living animal body, including a human, which disease or disorder is responsive to the action of a nicotinic Acetyl Choline Receptor (nAChR) modulator, which method comprises the step of administering to such a living animal body, including a human, in need thereof a therapeutically effective amount of the diazabicycloalkane derivative of the invention.

In a sixth aspect the invention relates to the use of the diazabicycloalkane derivative of the invention or any of its enantiomers or any mixture of enantiomers, in labelled or unlabelled form, for the manufacture of a diagnostic agent for the diagnosis of a disorder or disease of a living animal body, including a human, which disease or disorder is responsive to the action of a nicotinic Acetyl Choline Receptor (nAChR) modulator.

In a seventh aspect the invention provides a method for the non-invasive determination of the distribution of a tracer compound inside a whole, intact living animal or human body using a physical detection method, wherein the tracer compound is a diazabicycloalkane derivative of the invention, or any of its enantiomers or any mixture of enantiomers, or a pharmaceutically acceptable salt thereof, in labelled or unlabelled form.

DETAILED DISCLOSURE OF THE INVENTION

The present invention provides novel diazabicycloalkane derivatives, which derivatives may be characterised by the general Formula I

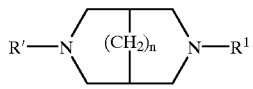

wherein n represents 0, 1 or 2;

R' represents hydrogen, an alkyl group, an aryl group, an aralkyl group or a fluorescent group; and $R^1$ represents a mono- or poly-heterocyclic group, which heterocyclic group may be substituted one or more times with substituents selected from the group consisting of alkyl, cycloalkyl, cycloalkylalkyl, alkenyl, alkynyl, methylenedioxy, hydroxy, alkoxy, alkoxy-alkyl, alkoxy-alkoxy, aryloxy, sulfhydryl, thioalkoxy, alkylcarbonyloxy, halogen, $CF_3$, $OCF_3$, CN, and nitro; or which heterocyclic group may be substituted once with another mono- or poly-heterocyclic group, a mono- or polycyclic aryl group, or a mono- or polycyclic aralkyl group; and/or which heterocyclic group may be substituted with one or more fluorescent groups.

In a preferred embodiment, the diazabicycloalkane derivative of the invention is a diazabicyclo[3.3.0]octane derivative of the general Formula II

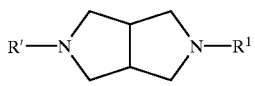

(II)

wherein R' and $R^1$ are as defined above.

in another preferred embodiment, the diazabicycloalkane derivative of the invention is a diazabicyclo[3.3.1] nonane derivative of the general Formula III

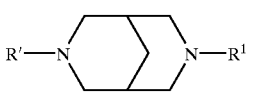

(III)

wherein R' and $R^1$ are as defined above.

in a third preferred embodiment, the diazabicycloalkane derivative of the invention is a diazabicyclo[3.3.2] decane derivative of the general Formula IV

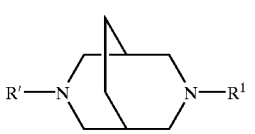

(IV)

wherein R' and $R^1$ are as defined above.

in a more preferred embodiment, the diazabicycloalkane derivative of the invention is a compound of Formula I, II, III or IV, wherein $R^1$ represents a monocyclic 5- or 6-membered, saturated, partially saturated or unsaturated heterocyclic group, which heterocyclic group may be substituted one or more times with substituents selected from the group consisting of alkyl, cycloalkyl, cycloalkylalkyl, alkenyl, alkynyl, methylenedioxy, hydroxy, alkoxy, alkoxy-alkyl, alkoxy-alkoxy, aryloxy, sulfhydryl, thioalkoxy, alkylcarbonyloxy, halogen, $CF_3$, $OCF_3$, CN, and nitro; or which heterocyclic group may be substituted once with another mono- or poly-heterocyclic group, a mono- or polycyclic aryl group, or a mono- or polycyclic aralkyl group; and/or which heterocyclic group may be substituted with one or more fluorescent groups.

In another preferred embodiment, the diazabicycloalkane derivative of the invention is a compound of Formula I, II, III or IV, wherein $R^1$ represents a pyridyl or a quinolinyl group, which heterocyclic group may be substituted one or more times with substituents selected from the group consisting of alkyl, alkynyl, alkoxy, thioalkoxy, halogen, a 5-membered heterocyclic group, or a phenyl group.

In a third preferred embodiment, the diazabicycloalkane derivative of the invention is a compound of Formula I, II, III or IV, wherein $R^1$ represents a 3-pyridyl group, substituted in position 5- or 6-substituted with substituents selected from the group consisting of $C_{1-3}$-alkyl, $C_{1-3}$-alkynyl, $C_{1-3}$-alkoxy, phenyl, 1-pyrrolyl, 1-indolyl, thioethoxy, or halogen.

In a most preferred embodiment the diazabicycloalkane derivative of the invention is a compound of Formula I, II, III or IV, wherein R' represents hydrogen, phenyl or benzyl.

In yet another preferred embodiment the diazabicycloalkane derivative of the invention is a compound of Formula I, II, III or IV, wherein $R^1$ represents a bi-cyclic heterocyclic group composed of a monocyclic 5- or 6-membered heterocyclic group with one heteroatom, fused to a benzene ring or fused to another monocyclic 5- or 6-membered, saturated, partially saturated or unsaturated heterocyclic group, which bi-cyclic heterocyclic group may be substituted one or more times with substituents selected from the group consisting of alkyl, cycloalkyl, cycloalkylalkyl, alkenyl, alkynyl, methylenedioxy, hydroxy, alkoxy, alkoxy-alkyl, alkoxy-alkoxy, aryloxy, sulfhydryl, thioalkoxy, alkylcarbonyloxy, halogen, $CF_3$, $OCF_3$, CN, and nitro; or which bi-cyclic heterocyclic group may be substituted once with a monocyclic aryl group; and/or which heterocyclic group may be substituted with one or more fluorescent groups.

The diazabicycloalkane derivatives of the invention may be provided in labelled or unlabelled form, or in any enantiomeric form or in any mixture of enantiomers, or in the form of a pharmaceutically acceptable salt or in the form of a prodrug.

In a most preferred embodiment, the diazabicycloalkane derivative of the invention is 3-(3-Pyridyl)-3,7-diazabicyclo[3.3.0]octane;

3-(5-Ethoxy-3-pyridyl)-3,7-diazabicyclo[3.3.0]octane;

3-(5-Phenyl-3-pyridyl)-3,7-diazabicyclo[3.3.0]octane;

3-[5-(1-Pyrrolyl)-3-pyridyl]-3,7-diazabicyclo[3.3.0] octane;

3-[5-(1-Indolyl)-3-pyridyl]-3,7-diazabicyclo[3.3.0] octane;

3-(5-Chloro-3-pyridyl)-3,7-diazabicyclo[3.3.0]octane;

3-(5-Bromo-3-pyridyl)-3,7-diazabicyclo[3.3.0]octane;

3-(5-Fluoro-3-pyridyl)-3,7-diazabicyclo[3.3.0]octane;

3-(5-Iodo-3-pyridyl)-3,7-diazabicyclo[3.3.0]octane;

3-(6-Thioethoxy-3-pyridyl)-3,7-diazabicyclo[3.3.0] octane;

3-(5-Thioethoxy-3-pyridyl)-3,7-diazabicyclo[3.3.0]octane;
3-(5-Trifluoromethyl-3-pyridyl)-3,7-diazabicyclo[3.3.0]octane;
3-(6-Fluoro-3-pyridyl)-3,7-diazabicyclo[3.3.0]octane;
3-(6-Chloro-3-pyridyl)-3,7-diazabicyclo[3.3.0]octane;
3-(6-Bromo-3-pyridyl)-3,7-diazabicyclo[3.3.0]octane;
3-(6-Iodo-3-pyridyl)-3,7-diazabicyclo[3.3.0]octane;
3-(5-Ethyl-3-pyridyl)-3,7-diazabicyclo[3.3.0]octane;
3-(5-Ethynyl-3-pyridyl)-3,7-diazabicyclo[3.3.0]octane;
3-(3-Pyridyl)-3,7-diazabicyclo[3.3.1]nonane;
3-(5-Ethoxy-3-pyridyl)-3,7-diazabicyclo[3.3.1]nonane;
3-(5-Chloro-3-pyridyl)-3,7-diazabicyclo[3.3.1]nonane;
3-(5-Bromo-3-pyridyl)-3,7-diazabicyclo[3.3.1]nonane;
3-(5-Fluoro-3-pyridyl)-3,7-diazabicyclo[3.3.1]nonane;
3-(5-Iodo-3-pyridyl)-3,7-diazabicyclo[3.3.1]nonane;
3-(5-Trifluoromethyl-3-pyridyl)-3,7-diazabicyclo[3.3.1]nonane;
3-(6-Fluoro-3-pyridyl)-3,7-diazabicyclo[3.3.1]nonane;
3-(6-Chloro-3-pyridyl)-3,7-diazabicyclo[3.3.1]nonane;
3-(6-Bromo-3-pyridyl)-3,7-diazabicyclo[3.3.1]nonane;
3-(6-Iodo-3-pyridyl)-3,7-diazabicyclo[3.3.1]nonane;
3-(5-Ethyl-3-pyridyl)-3,7-diazabicyclo[3.3.1]nonane;
3-(5-Ethynyl-3-pyridyl)-3,7-diazabicyclo[3.3.1]nonane;
7-Benzyl-3-(2-quinolinyl)-3,7-diazabicyclo[3.3.1]nonane;
7-H-3-(2-Quinolinyl)-3,7-diazabicyclo[3.3.1]nonane;
3-(3-Pyridyl)-3,7-diazabicyclo[3.3.2]decane;
3-(5-Ethoxy-3-pyridyl)-3,7-diazabicyclo[3.3.2]decane;
3-(5-Chloro-3-pyridyl)-3,7-diazabicyclo[3.3.2]decane;
3-(5-Bromo-3-pyridyl)-3,7-diazabicyclo[3.3.2]decane;
3-(5-Fluoro-3-pyridyl)-3,7-diazabicyclo[3.3.2]decane;
3-(5-Iodo-3-pyridyl)-3,7-diazabicyclo[3.3.2]decane;
3-(5-Trifluoromethyl-3-pyridyl)-3,7-diazabicyclo[3.3.2]decane;
3-(6-Fluoro-3-pyridyl)-3,7-diazabicyclo[3.3.2]decane;
3-(6-Chloro-3-pyridyl)-3,7-diazabicyclo[3.3.2]decane;
3-(6-Bromo-3-pyridyl)-3,7-diazabicyclo[3.3.2]decane; or
3-(6-Iodo-3-pyridyl)-3,7-diazabicyclo[3.3.2]decane;
in labelled or unlabelled form, or any of its enantiomers or any mixture of enantiomers, or a pharmaceutically acceptable salt thereof or a prodrug thereof.

Definition of Substituents

In the context of this invention halogen represents a fluorine, a chlorine, a bromine or an iodine atom. Thus, a trihalogenmethyl group represents e.g. a trifluoromethyl group and a trichloromethyl group.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1,2- or 2,3-propenyl; or 1,2-, 2,3-, or 3,4-butenyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl, 1,2- or 2,3-propynyl, 1,2-, 2,3- or 3,4-butynyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above.

In the context of this invention an alkoxy-alkyl group designates an "alkyl-O-alkyl-" group, wherein alkyl is as defined above.

In the context of this invention an alkoxy-alkoxy group designates an "alkyl-O-alkyl-O—" group, wherein alkyl is as defined above.

In the context of this invention sulfhydryl designates a —SH group (sulfanyl or mercapto).

In the context of this invention an thioalkoxy group designates an "alkyl-S—" (alkylthio) group, wherein alkyl is as defined above. Likewise thioalkoxy-alkoxy, alkoxy-thioalkoxy, and thioalkoxy-thioalkoxy designates a thioalkoxy group as defined above, attached to another thioalkoxy group, or to an alkoxy group as defined above.

In the context of this invention an alkylcarbonyloxy group designates an "alkyl-CO—O—" group, wherein alkyl is as defined above.

In the context of this invention a mono- or polycyclic aryl group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention an aralkyl group designates a mono- or polycyclic aryl group as defined above, which aryl group is attached to an alkyl group as also defined above. A preferred aralkyl group of the invention is benzyl.

In the context of this invention an aryloxy group designates an "aryl-O—" group, wherein aryl is a mono- or polycyclic aryl group as defined above.

In the context of this invention a mono-, bi- or poly-heterocyclic group is a mono- or polycyclic compound, which holds one or more heteroatoms in its ring structure. Preferred heteroatoms include nitrogen (N), oxygen (O), and sulphur (S). One or more of the ring structures may in particular be aromatic or partially saturated (i.e. a heteroaryl), or fully saturated.

Preferred heterocyclic monocyclic groups of the invention include 5- and 6-membered heterocyclic monocyclic groups.

Examples of preferred aromatic heterocyclic monocyclic groups of the invention include 1,3,2,4- or 1,3,4,5-dioxadiazolyl, dioxatriazinyl, dioxazinyl, 1,2,3-, 1,2,4-, 1,3, 2- or 1,3,4-dioxazolyl, 1,3,2,4- or 1,3,4,5-dithiadiazolyl, dithiatriazinyl, dithiazinyl, 1,2,3-dithiazolyl, 2- or 3-furanyl, furazanyl, 1,2 or 4-imidazolyl, isoindazolyl, isothiazol-3,4 or 5-yl, isoxazol-3,4 or 5-yl, 1,2,3-, 1,2,4-, 1,2,5- or 1,3,4-oxadiazol-3,4 or 5-yl, oxatetrazinyl, oxatriazinyl, 1,2,3,4- or 1,2,3,5-oxatriazolyl, oxazol-2,4 or 5-yl, 2 or 3-pyrazinyl, 1,3 or 4-pyrazolyl, 3 or 4-pyridazinyl, 2,3 or 4-pyridinyl, 2,4 or 5-pyrimidinyl, 1,2 or 3-pyrrolyl (azolyl), 1,2,3,4- or 2,1,3, 4-tetrazolyl, thiadiazol-3,4 or 5-yl, thiazol-2,4 or 5-yl, 2 or 3-thienyl, 1,2,3-, 1,2,4- or 1,3,5-triazinyl, and 1,2,3-, 1,2,4-, 2,1,3- or 4,1,2-triazolyl. Most preferred heterocyclic monocyclic groups of the invention include 1,2 or 3-pyrrolyl (azolyl), and 1-, 2- or 3-pyridinyl.

Examples of preferred saturated or partially saturated heterocyclic monocyclic groups of the invention include 1,3,5,6,2-dioxadiazinyl, 1,2,3,4,5-, 1,2,3,5,4-dioxadiazolyl, dioxanyl, 1,3-dioxolyl, 1,3,5,6,2-dithiadiazinyl, 1,2,3,4,5- or 1,2,3,5,4-dithiadiazolyl, 2-isoimidazolyl, isopyrrolyl, isotetrazolyl, 1,2,3- or 1,2,4-isotriazolyl, morpholinyl, oxadiazinyl, 1,2,4-, 1,2,6-, 1,3,2-, 1,3,6- or 1,4,2-oxazinyl, piperazinyl, homopiperazinyl, piperidinyl, 1,2-, 1,3- or 1,4-pyranyl, and 1,2,3-pyrrolidinyl.

Examples of preferred bicyclic heteroaryl groups of the invention include benzimidazolyl, in particular 2,5 or 6-benzimidazolyl; 1,3-benzisodiazolyl, in particular 1,3-benzisodiazol-2,5 or 6-yl; 1,2- or 1,4-benzisothiazinyl, in particular 1,2- or 1,4-benzisothiazin-2,3,6 or 7-yl; 1,2- or 1,4-benzisoxazinyl, in particular 1,2- or 1,4-benzisoxazin-2,3,6 or 7-yl; 1,2- or 1,4-benzopyranyl, in particular 1,2- or 1,4-benzopyran-2,3,6 or 7-yl; 1,3,2-, 1,4,2-, 2,3,1- or 3,1,4-benzoxazinyl, in particular 1,3,2-, 1,4,2-, 2,3,1- or 3,1,4-benzoxazin-2,3,6 or 7-yl; benzofuranyl, in particular 2,5 or 6-benzofuranyl; isobenzofuranyl, in particular 5 or 6-isobenzofuranyl; benzothiazolyl, in particular 5 or 6-benzothiazolyl; benzothienyl, in particular 2,5 or 6-benzothienyl; benzotrizolyl, in particular 5 or 6-benzotrizolyl; chromanyl, in particular 2,3,6 or 7-chromanyl; 4H-chromenyl, in particular 2,3,6 or 7-chromenyl; cinnolinyl, in particular 6 or 7-cinnolinyl; indanyl, in particular 2,5 or 6-indanyl; indazolyl, in particular 2,5 or 6-indazolyl; 1H-indazolyl, in particular 1H-indazol-2,5 or 6-yl; indolyl, in particular 2,5 or 6-indolyl; isoindolyl, in particular 2,5 or 6-isoindolyl; 3H-indolyl, in particular 3H-indol-2,5 or 6-yl; indolinyl, in particular 2,5 or 6-indolinyl; indolizinyl, in particular 2,5 or 6-indolizinyl; 1,8-naphthyridinyl, in particular 1,8-naphthyridin-2,3,6 or 7-yl; phthalazinyl, in particular 6 or 7-phthalazinyl; purinyl, in particular 2 or 8-purinyl; pteridinyl, in particular 2,6 or 7-pteridinyl; quinolinyl, in particular 2,3,6 or 7-quinolinyl; isoquinolinyl, in particular 3,6 or 7-isoquinolinyl; quinazolinyl, in particular 2,6 or 7-quinazolinyl; 4H-quinolizinyl, in particular 4H-quinazolin-2,3,7 or 8-yl; and quinoxalinyl, in particular 2 or 6-quinoxalinyl.

Most preferred bicyclic heteroaryl groups of the invention include indolyl, in particular 2,5 or 6-indolyl.

In the context of this invention a hetero-alkyl group designates a mono- or poly-heterocyclic group as described above, which heterocyclic group is attached to an alkyl group as also defined above. Examples of preferred heteroalkyl groups of the invention include furfuryl and picolyl.

In the context of this invention a fluorescent group is a functional group which can be detected by spectroscopic methods and may be selected from the group of naturally occurring fluorophores or chemically synthesized fluorescent groups, such as rhodamine, green fluorescent protein or fluorescein and its derivatives.

Pharmaceutically Acceptable Salts

The diazabicycloalkane derivatives of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a diazabicycloalkane derivative of the invention and its pharmaceutically acceptable acid addition salt.

Metal salts of the diazabicycloalkane derivative of the invention includes the alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The diazabicycloalkane derivatives of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

The diazabicycloalkane derivatives of the present invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The diazabicycloalkane derivatives of the invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Optical active compounds can also be prepared from optical active starting materials.

Prodrugs

The diazabicycloalkane derivatives of the invention may be administered as such or in the form of a suitable prodrug. The term "prodrug" denotes a bioreversible derivative of the drug, the bioreversible derivative being therapeutically substantially inactive per se but being able to convert in the body to the active substance by an enzymatic or non-enzymatic process.

Thus examples of suitable prodrugs of the diazabicycloalkane derivatives of the invention include compounds obtained by suitable bioreversible derivatization of one or more reactive or derivatizable groups of the parent substance to result in a bioreversible derivative. The derivatization may be performed to obtain a higher bioavailability of the active substance, to stabilize an otherwise unstable active substance, to increase the lipophilicity of the substance administered, etc.

Examples of types of chemical substances, which may advantageously be administered in the form of prodrugs, are carboxylic acids, other acidic groups and amines, which may be rendered more lipophilic by suitable bioreversible derivatization. Examples of suitable groups include bioreversible esters or bioreversible amides. Amino acids are typical examples of substances, which, in their unmodified form, may have a low absorption upon administration. Suitable prodrug derivatives of amino acids will be one or both of the above-mentioned types of bioreversible derivatives.

Method of Producing the Compounds

The diazabicycloalkane derivatives of the invention may be prepared by any conventional method useful for the preparation of analogous compounds and as described in the examples below.

Starting materials for the processes described herein are known or can be prepared by known processes from commercially available materials, e.g. as described in the working examples.

Also, one diazabicycloalkane derivative of the invention can be converted to another compound of the invention using conventional methods.

Biological Activity

The diazabicycloalkane derivatives of the present invention are nicotinic receptor modulators. In the context of this invention the term "modulator" covers agonists, partial agonists, antagonists and allosteric modulators of the nicotinic acetyl choline receptor (nAChR).

The compounds of the present invention exhibit a nicotinic pharmacology at least as good as nicotine itself, but preferably with lesser or even without the side effects associated with the use of nicotine. Moreover, the compounds of the invention are believed to have the potential as enhancers of neurotransmitter secretion, and suppress symptoms associated with a low activity of neurotransmitters.

The compounds of the present invention may in particular be characterised by having one or more of the following functionalities: A high binding selectivity for the receptor subtypes of neuronal nAChR's, in particular the $\alpha 3$, $\alpha 4$ and/or the $\alpha 7$ subtype, binding selectivity for the serotonin receptor, a low affinity for the muscular subtype, an induction of cell survival, an oral efficacy in vivo of arousal/attention, a low toxicity in vivo, and by being non-mutagenic.

Due to their pharmacological profile the compounds of the invention may be useful for the treatment of diseases or conditions as diverse as CNS related diseases, diseases related to smooth muscle contraction, endocrine disorders, diseases related to neurodegeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourettes syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, chronic fatigue syndrome, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neurodegeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

Neuroimaging

The diazabicycloalkane derivatives of the invention, in particular those being selective for the nicotinic receptor subtype α3, α4 and/or α7 may be useful as diagnostic tools or monitoring agents in various diagnostic methods, and in particular for in vivo receptor imaging (neuroimaging).

In another aspect of the invention a method for the non-invasive determination of the distribution of a tracer compound inside a whole, intact living animal or human body using a physical detection method is provided. According to this method a tracer compound is a compound of the invention, or any of its enantiomers or any mixture of enantiomers, or a pharmaceutically acceptable salt thereof, in labelled or unlabelled form.

In a preferred embodiment the physical detection method is selected from PET, SPECT; MRS, MRI, CAT, or combinations thereof.

The compounds of the invention may be used in their labelled or unlabelled form. In the context of this invention "label" stands for the binding of a marker to the compound of interest that will allow easy quantitative detection of said compound.

The labelled compound of the invention preferably contains at least one radionuclide as a label. Positron emitting radionuclides are all candidates for usage. In the context of this invention the radionuclide is preferably selected from $^{11}C$, $^{18}F$, $^{15}O$, $^{13}N$, $^{123}I$, $^{125}I$, $^{131}I$, $^{3}H$ and $^{99m}Tc$.

Examples of commercially available labelling agents, which can be used in the preparation of the labelled compounds of the present invention are $[^{11}C]O_2$, $^{18}F$, and NaI with different isotopes of Iodine. In particular $[C^{11}]O_2$ may be converted to a $[^{11}C]$-methylating agent, such as $[^{11}C]H_3I$ or $[^{11}C]$-methyl triflate.

Labelled compounds containing e.g. $[^{125}I]$ labelled 1-iodoprop-1-en-3-yl as substituent on N-8 may be prepared as described in the art [Elmaleh, et al.; J. Nucl. Med. 1996 37 1197–1202].

Labelled compounds containing e.g. $[^{18}F]$-alkyl substituted N-8 may be prepared as described in the art, e.g. in WO 96/39198.

The tracer compound can be selected in accordance with the detection method chosen.

In one preferred embodiment, the labelled or unlabelled compound of the invention can be detected by a suitable spectroscopic method, in particular UV spectroscopy and/or fluorescence spectroscopy.

In anther preferred embodiment, the compounds of the invention labelled by incorporation of a isotope into the molecule, which may in particular be an isotope of the naturally occurring atoms including deuterium, tritium, $^{13}C$, $^{14}C$, $^{131}I$, $^{125}I$, $^{123}I$, and $^{18}F$, the isotope incorporation may be measured by conventional scintillation counting techniques.

In a third preferred embodiment, the physical method for detecting said tracer compound of the present invention is selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Before conducting the method of the present invention, a diagnostically effective amount of a labelled or unlabelled compound of the invention is administered to a living body, including a human.

The diagnostically effective amount of the labelled or unlabelled compound of the invention to be administered before conducting the in-vivo method for the present invention is within a range of from 0.1 ng to 100 mg per kg body weight, preferably within a range of from 1 ng to 10 mg per kg body weight.

Pharmaceutical Compositions

In another aspect the invention provides novel pharmaceutical compositions comprising a therapeutically effective amount of the diazabicycloalkane derivative of the invention.

While a diazabicycloalkane derivative of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicycloalkane derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The diazabicycloalkane derivative of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The diazabicycloalkane derivative of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a diazabicycloalkane derivative of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The diazabicycloalkane derivative of the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, which are intended to be converted shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the diazabicycloalkane derivative may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatine and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatine, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.01 to about 500 mg of active ingredient per individual dose, preferably of from about 0.1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.01 $\mu$g/kg i.v. and 0.1 $\mu$g/kg p.o. The upper limit of the dosage range is presently considered to be about 10 mg/kg i.v. and 100 mg/kg p.o. Preferred ranges are from about 0.1 $\mu$g/kg to about 10 mg/kg/day i.v., and from about 1 $\mu$g/kg to about 100 mg/kg/day p.o.

Methods of Therapy

The compounds of the present invention are valuable nicotinic ACh receptor modulators and therefore useful for the treatment of a range of ailments involving cholinergic dysfunction as well as a range of disorders responsive to the action of nicotinic ACh receptor modulators as well as the serotonin receptor.

In another aspect the invention relates to the a method of the treatment or alleviation of a disease, disorder or condition of a living animal body, including a human, which disease, disorder or condition is responsive to the action of a nicotinic Acetyl Choline Receptor (nAChR) modulator, which method comprises the step of administering to such a living animal body, including a human, in need thereof a therapeutically effective amount of the chemical compound of the invention.

In the context of this invention the term "treating" covers treatment, prevention, prophylaxis or alleviation, and the term "disease" covers illnesses, diseases, disorders and conditions related to the disease in question.

In a preferred embodiment the disease or disorder to be treated is a disease or disorder of the central nervous system, a disease or disorder caused by or related to smooth muscle contraction, an endocrine disorder, a disease or disorder caused by or related to neuro-degeneration, a disease or disorder caused by or related to inflammation, pain, a withdrawal symptom caused by the termination of abuse of chemical substances.

In a more preferred embodiment the disease or disorder of the central nervous system is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourettes syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, chronic fatigue syndrome, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the disease or disorder caused by or related to smooth muscle contraction is a convulsive disorder, angina pectoris, premature labour, convulsions, diarrhoea, asthma, epilepsy, tardive dyskinesia, hyperkinesia, premature ejaculation, and erectile difficulty.

In a third preferred embodiment the endocrine disorder is thyrotoxicosis, pheochromocytoma, hypertension and arrhythmias.

In a fourth preferred embodiment the neuro-degenerative disease is transient anoxia and induced neurodegeneration.

In a fifth preferred embodiment the disease or disorder caused by or related to inflammation is an inflammatory skin disorder such as acne and rosacea, Chron's disease, inflammatory bowel disease, ulcerative colitis, and diarrhoea.

In a sixth preferred embodiment pain is a mild, a moderate or a severe pain of acute, chronic or recurrent character, a pain caused by migraine, a postoperative pain, or a phantom limb pain.

In a third preferred embodiment the addictive substance is a nicotine containing product such as tobacco, an opioids such as heroin, cocaine or morphine, a benzodiazepine or a benzodiazepin-like drug, or alcohol.

It is at present contemplated that a suitable dosage lies within the range of from about 0.1 to about 500 milligram of active substance daily, more preferred of from about 10 to about 70 milligram of active substance daily, administered once or twice a day, dependent as usual upon the exact mode of administration, form in which administered, the indication toward which the administration is directed, the subject involved and the body weight of the subject involved, and further the preference and experience of the physician or veterinarian in charge.

EXAMPLE

The invention is further illustrated with reference to the following examples, which are not intended to be in any way limiting to the scope of the invention as claimed.

General

All reactions involving air sensitive reagents or intermediates are performed under nitrogen and in anhydrous solvents. Magnesium sulphate is used as drying agent in the workup-procedures and solvents are evaporated under reduced pressure. The products are normally isolated as salts by stirring the free base with an excessive amount of a saturated solution of fumaric acid salt in a mixture of methanol and diethyl ether (1:9).

Workup-Procedure A

The crude reaction mixture was combined with aqueous sodium hydroxide and extracted with diethyl ether followed by column chromatography using silica gel as solid phase and a mixture of dichloromethane, methanol and aqueous ammonia as liquid phase.

Workup-Procedure B

The crude reaction mixture was combined with diluted aqueous hydrochloric acid so the pH was adjusted to 7. The impurities were removed by extraction by diethyl ether. Aqueous sodium hydroxide was added and the mixture was extracted with diethyl ether.

Method A 3-(3-Pyridyl)-3,7-diazabicyclo[3.3.0]octane (Compound A1):

Prepared by heating 3-fluoropyridine and 3.7-Diazabicyclo[3.3.0]octane in an autoclave in the absence of solvent at 180° C. for 24 hours. Workup-procedure A/B.

3-(3-Pyridyl)-3,7-diazabicyclo[3.3.1]nonane (Compound A2):

Obtainable according to method A.

3-(3-Pyridyl)-3,7-diazabicyclo[3.3.2]decane (Compound A3):

Obtainable according to method A.

Method B 3-(5-Ethoxy-3-pyridyl)-3,7-diazabicyclo[3.3.0]octane (Compound B1):

Obtainable by stirring a mixture of 3-chloro-5-ethoxypyridine (1 eq.), 3.7-Diazabicyclo[3.3.0]octane (1 eq.), potassium-tert-butoxide (2 eq.) and 1.2-dimethoxyethane as solvent. Workup-procedure A/B.

3-(5-Ethoxy-3-pyridyl)-3,7-diazabicyclo[3.3.1]nonane (Compound B2):

Obtainable according to method B.

3-(5-Ethoxy-3-pyridyl)-3,7-diazabicyclo[3.3.2]decane (Compound B3):

Obtainable according to method B.

3-(5-Phenyl-3-pyridyl)-3,7-diazabicyclo[3.3.0]octane (Compound B4):

Obtainable according to method B.

3-[5-(1-Pyrrolyl)-3-pyridyl]-3,7-diazabicyclo[3.3.0]octane (Compound B5):

Obtainable according to method B.

3-[5-(1-Indolyl)-3-pyridyl]-3,7-diazabicyclo[3.3.0]octane (Compound B6):

Obtainable according to method B.

Method C 3-(5-Chloro-3-pyridyl)-3,7-diazabicyclo[3.3.0]octane (Compound C1):

3,5-Dichloropyridine (1 eq.), 3.7-Diazabicyclo[3.3.0]octane (1 eq.) and palladacycle (0.2%) [Herrmann W A, Brossmer C, Öfele K, Reisinger, C-P, Priermeier, T, Beller M, and Fischer, H; Angew. Chem. Int. Ed. Enql. 1995 34 1844] is stirred at 160° C. for 24 hours. Workup-procedure A/B.

3-(5-Bromo-3-pyridyl)-3,7-diazabicyclo[3.3.0]octane (Compound C2):

Obtainable according to method C.

3-(5-Fluoro-3-pyridyl)-3,7-diazabicyclo[3.3.0]octane (Compound C3):

Obtainable according to method C.

3-(5-Iodo-3-pyridyl)-3,7-diazabicyclo[3.3.0]octane (Compound C4):

Obtainable according to method C.

3-(6-Thioethoxy-3-pyridyl)-3,7-diazabicyclo[3.3.0]octane (Compound C5):

Obtainable according to method C.

3-(5-Thioethoxy-3-pyridyl)-3,7-diazabicyclo[3.3.0]octane (Compound C6):

Obtainable according to method C.

3-(5-Chloro-3-pyridyl)-3,7-diazabicyclo[3.3.1]nonane (Compound C7):

Obtainable according to method C.

3-(5-Bromo-3-pyridyl)-3,7-diazabicyclo[3.3.1]nonane (Compound C8):

Obtainable according to method C.

3-(5-Fluoro-3-pyridyl)-3,7-diazabicyclo[3.3.1]nonane (Compound C9):

Obtainable according to method C.

3-(5-Iodo-3-pyridyl)-3,7-diazabicyclo[3.3.1]nonane (Compound C10):

Obtainable according to method C.

3-(5-Chloro-3-pyridyl)-3,7-diazabicyclo[3.3.2]decane (Compound C11):

Obtainable according to method C.

3-(5-Bromo-3-pyridyl)-3,7-diazabicyclo[3.3.2]decane (Compound C12):

Obtainable according to method C.

3-(5-Fluoro-3-pyridyl)-3,7-diazabicyclo[3.3.2]decane (Compound C13):

Obtainable according to method C.

3-(5-Iodo-3-pyridyl)-3,7-diazabicyclo[3.3.2]decane (Compound C14):

Obtainable according to method C.

3-(5-Trifluoromethyl-3-pyridyl)-3,7-diazabicyclo[3.3.0]octane (Compound C15):

Obtainable according to method C.

3-(5-Trifluoromethyl-3-pyridyl)-3,7-diazabicyclo[3.3.1]nonane (Compound C16):

Obtainable according to method C.

3-(5-Trifluoromethyl-3-pyridyl)-3,7-diazabicyclo[3.3.2]decane (Compound C17):

Obtainable according to method C.

The following compounds are obtainable from the compounds described above:

3-(6-Fluoro-3-pyridyl)-3,7-diazabicyclo[3.3.0]octane (Compound C18);

3-(6-Chloro-3-pyridyl)-3,7-diazabicyclo[3.3.0]octane (Compound C19);

3-(6-Bromo-3-pyridyl)-3,7-diazabicyclo[3.3.0]octane (Compound C20);

3-(6-Iodo-3-pyridyl)-3,7-diazabicyclo[3.3.0]octane (Compound C21);

3-(6-Fluoro-3-pyridyl)-3,7-diazabicyclo[3.3.1]nonane (Compound C22);

3-(6-Chloro-3-pyridyl)-3,7-diazabicyclo[3.3.1]nonane (Compound C23);

3-(6-Bromo-3-pyridyl)-3,7-diazabicyclo[3.3.1]nonane (Compound C24);

3-(6-Iodo-3-pyridyl)-3,7-diazabicyclo[3.3.1]nonane (Compound C25);

3-(6-Fluoro-3-pyridyl)-3,7-diazabicyclo[3.3.2]decane (Compound C26);

3-(6-Chloro-3-pyridyl)-3,7-diazabicyclo[3.3.2]decane (Compound C27);

3-(6-Bromo-3-pyridyl)-3,7-diazabicyclo[3.3.2]decane (Compound C28);

3-(6-Iodo-3-pyridyl)-3,7-diazabicyclo[3.3.2]decane (Compound C29);

3-(5-Ethyl-3-pyridyl)-3,7-diazabicyclo[3.3.0]octane (Compound C30);

3-(5-Ethynyl-3-pyridyl)-3,7-diazabicyclo[3.3.0]octane (Compound C31);

3-(5-Ethyl-3-pyridyl)-3,7-diazabicyclo[3.3.1]nonane (Compound C32); and 3-(5-Ethynyl-3-pyridyl)-3,7-diazabicyclo[3.3.1]nonane (Compound C33).

Method D

7-Benzyl-3-(2-quinolinyl)-3,7-diazabicyclo[3.3.1]nonane (Compound D1):

A mixture of 3,7-dibenzyl-3.7-diazabicyclo[3.3.1] nonane-9-one [Garrison G L et. al.; *J. Org. Chem.* 1993 58 7670–7678] (3.8 g, 11.4 mmol), hydrazine hydrate (4.26 ml, 137 mmol), potassium hydroxide (3.8 g, 68 mmol), diethyleneglycol (100 ml) and 1.3.5-trimethylbenzene (250 ml) was stirred and heated at 203° C. overnight with a Dean & Stark water collector.

The mixture was allowed to reach room temperature. Sodium hydroxide (200 ml, 1 M) was added and the mixture was extracted twice with diethyl ether (2×100 ml). The organic phase was washed with aqueous sodium hydroxide (2×100 ml, 1 M).

The crude product of 3,7-dibenzyl-3,7-diazabicyclo [3.3.1]nonane was 77% pure according to GC-MS-analysis.

The crude mixture of 3,7-dibenzyl-3.7-Diazabicyclo [3.3.1]nonane, formic acid (2.16 ml, 57 mmol), palladium on carbon (5.0 g, 10%) was stirred until the theoretical amount of hydrogen was consumed. The crude mixture was evaporated to dryness. The resulting crude mixture of 3-benzyl-7-H-3,7-diazabicyclo[3.3.1]nonane and 2-chloroquinoline (0.67 g, 4.1 mmol) at 100° C. for 1 hour after cooling to room temperature. Dichloromethane (50 ml) was added. The organic phase was extracted twice with hydrochloric acid (2×25 ml, 1 M). The aqueous phase was made alkaline by adding aqueous sodium hydroxide (50 ml, 4 M), followed by extraction twice with dichloromethane (2×25 ml).

Chromatography on silica gel with dichloromethane, methanol and conc. ammonia (89:10:1) gave the title compound as an oil. Yield 0.28 g, 7%.

The corresponding salt was obtained by addition of a diethyl ether and methanol mixture (9:1) saturated with fumaric acid.

1H-NMR (fumaric acid salt product): δ 8.01 (d, 1H), δ 7.69 (d, 1H), δ 7.56–7.48 (m, 2 H), δ 7.20–7.15 (m, 2 H), δ 7.08–7.03 (m, 1 H), δ 6.95–6.86 (m, 4 H), δ 6.60 (fumaric acid salt), δ 4.40 (s, broad, 2 H), δ 3.35 (s, 2 H), δ 3.22 (d, 2 H), δ 2.98 (d, 2 H), 2.36 (d, broad, 2 H), δ (s, 2H), δ 1.84 (d, broad, 1H), δ 1.69 (d, broad, 1 H) ppm. Mp 56.1–56.8° C.

7-H-3-(2-Quinolinyl)-3,7-diazabicyclo[3.3.1]nonane (Compound D2):

7-Benzyl-3-(2-quinolinyl)-3,7-diazabicyclo[3.3.1]nonane (0.18 g, 0.52 mmol) and palladium on carbon (0.5 g, 10%) was stirred under hydrogen overnight. The crude mixture was was filtered.

Chromatography on silica gel with dichloromethane, methanol and conc. ammonia (89:10:1) gave the title compound as an oil.

1H-NMR (product as free base): δ 7.88 (d, 1 H), δ 7.73 (d, 1 H), δ 7.62 (d, 1 H), δ 7.54 (dd, 1 H), δ 7.19 (dd, 1 H), δ 7.01 (d, 1 H), δ 4.32 (d, 2 H), δ 3.45 (d, 2 H), δ 3.05 (s, 2 H), δ 2.3–2.10 (m, 3 H), δ 1.85 (d, 1 H), δ 1.75 (s, broad, 1 H), δ 0.87 (s, 2 H) ppm.

The corresponding salt was obtained by addition of a diethyl ether and methanol mixture (9:1) saturated with fumaric acid.

Starting Materials 3.7-Diazabicyclo[3.3.0]octane:

Obtainable according to Weinges & Spänig [Weinges K & Spänig R; *Chem. Ber.* 1968 101 3010–3017] and Ohnmacht et al. [Ohnmacht C J, Draper C W, Dedinas R F, Loftus P & Wong J J; *J. Heterocycl. Chem.* 1983 20 321–329].

3.7-Diazabicyclo[3.3.1]nonane:

Obtainable by catalytic hydrogenation of 3,7-dibenzyl-3.7-diazabicyclo[3.3.1]nonane. Hydrogenation is performed by stirring 3,7-dibenzyl-3.7-diazabicyclo[3.3.1]nonane in a mixture of ethanol, concentrated hydrochloric acid and palladium on carbon under an atmosphere of hydrogen.

3,7-Dibenzyl-3.7-diazabicyclo[3.3.1]nonane:

Obtainable by the same procedure as used for the preparation of 3,7-dimethyl-3.7-diazabicyclo[3.3.1]nonane according to Douglass & Ratliff [Douglass J E D & Ratliff T B; *J. Org. Chem.* 1968 33 355–359].

3-Bromo-5-phenylpyridine:

A mixture of 3,5-dibromopyridine (10.0 g, 42.2 mmol), phenylboronic acid (4.6 g, 38.0 mmol), tetrakis (triphenylphosphine)palladium(0) (1.45 g, 1.25 mmol), potassium carbonate (17.5 g, 127 mmol), water (63 ml) and 1,2-dimethoxyethane (126 ml) was stirred at reflux overnight. Aqueous sodium hydroxide (1 M, 60 ml) was added followed by extraction twice with diethyl ether (100 ml). Chromatography on silica gel with dichloromethane as solvent gave the title compound. Yield 6.1 g, 68%, Mp 42–44° C.

3-Bromo-6-thioethoxypyridine:

A mixture of sodium thioethoxide (7.81 g, 92.9 mmol), 2.5-dibromopyridine (20.0 g, 84.4 mmol) and dimethyl sulfoxide (100 ml). The mixture was stirred at 20° C. overnight. Sodium hydroxide (300 ml, 1 M) was added and the mixture was extracted twice with diethyl ether (200 ml). Chromatography on silica gel with dichloromethane: petroleum ether, 1:2 as eluent, gave the title compound as an oil. Yield 16.8 g, 85%.

3-Bromo-5-thioethoxypyridine:

Prepared according to 3-Bromo-6-thioethoxypyridine, using 40° C. as reaction temperature.

The title compound was obtained as an oil.

3-Chloro-5-ethoxylpyridine:

Prepared according to 3-Bromo-6-thioethoxypyridine, using 60° C. as reaction temperature.

The title compound was obtained as an oil.

3-Chloro-5-(1-pyrrolyl)-pyridine:

A mixture of 3.5 dichloropyridine (10.0 g, 67.6 mmol), pyrrole (5.50 g, 81.1 mmol), sodium hydride 60% (3.52 g, 87.9 mmol) and dimethyl sulfoxide (50 ml) was stirred at 70° C. for 2 hours. Aqueous sodium hydroxide (200 ml, 1 M) was added and the mixture was extracted three times with diethyl ether (100 ml). The mixture was evaporated and purified by chromatography on silica gel with dichloromethane and ethanol (4%) as solvent. Yield 6.3 g, 52%. Mp 70.5–72.0° C.

3-Chloro-5-(1-indolyl)-pyridine:

Was prepared according to 3-Chloro-5-(1-pyrrolyl)-pyridine. Yield 5.9 g, 38%. Mp 56–57° C.

What is claimed is:

1. A diazabicycloalkane compound of Formula I

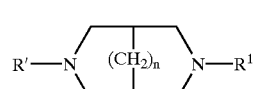

(I)

any of its enantiomers or any mixture of enantiomers, or a pharmaceutically acceptable salt thereof or a prodrug thereof;

wherein n represents 1;

R' represents hydrogen or a $C_{1-6}$-alkyl group; and

R$^1$ represents a pyridyl or a quinolinyl group, which may be substituted by one or more substituents selected from the group consisting of halogen, $CF_3$, $C_{1-6}$-alkyl, $C_{1-6}$-alkynyl, $C_{1-6}$-alkoxy, $C_{1-6}$-thioalkoxy, phenyl, naphthyl, 1-pyrrolyl, or 1-indolyl.

2. The diazabicycloalkane compound of claim 1, wherein R$^1$ represents a 3-pyridyl group, which pyridyl is substituted at positions 5 or 6 with substituents selected from the group consisting of halogen, $CF_3$, $C_{1-3}$-alkyl, $C_{1-3}$-alkynyl, $C_{1-3}$-alkynyl, $C_{1-3}$-alkoxy, $C_{1-3}$-thioalkoxy, phenyl, naphthyl, 1-pyrrolyl, or 1-indolyl.

3. The diazabicycloalkane compound of claim 1 which is 3-(5-Ethoxy-3-pyridyl)-3,7-diazabicyclo[3.3.1]nonane;

3-(5-Chloro-3-pyridyl)-3,7-diazabicyclo[3.3.1]nonane;

3-(5-Bromo-3-pyridyl)-3,7-diazabicyclo[3.3.1]nonane;

3-(5-Fluoro-3-pyridyl)-3,7-diazabicyclo[3.3.1]nonane;

3-(5-Iodo-3-pyridyl)-3,7-diazabicyclo[3.3.1]nonane;

3-(5-Trifluoromethyl-3-pyridyl)-3,7-diazabicyclo[3.3.1]nonane;

3-(6-Fluoro-3-pyridyl)-3,7-diazabicyclo[3.3.1]nonane;

3-(6-Chloro-3-pyridyl)-3,7-diazabicyclo[3.3.1]nonane;

3-(6-Bromo-3-pyridyl)-3,7-diazabicyclo[3.3.1]nonane;

3-(6-Iodo-3-pyridyl)-3,7-diazabicyclo[3.3.1]nonane;

3-(5-Ethy-3-pyridyl)-3,7-diazabicyclo[3.3.1]nonane;

3-(5-Ethynyl-3-pyridyl)-3,7-diazabicyclo[3.3.1]nonane;

7-Benzyl-3-(2-quinolinyl)-3,7-diazabicyclo[3.3.1]nonane; or

7-H-3-(2-Quinolinyl)-3,7-diazabicyclo[3.3.1]nonane;

any of its enantiomers or any mixture of enantiomers, or a pharmaceutically acceptable salt thereof or a prodrug thereof.

4. A pharmaceutical composition comprising a therapeutically effective amount of the diazabicycloalkane compound of claim 1, or a pharmaceutically acceptable addition salt thereof, together with at least one pharmaceutically acceptable carrier or diluent.

5. A method of the treatment of a disease or disorder of a mammal, which disease or disorder is a disease or disorder related to a withdrawal symptom caused by the termination of abuse of chemical substance, which method comprises the step of administering to such a mammal in need thereof a therapeutically effective amount of the diazabicycloalkane compound according to claim 1.

6. The method according to claim 5, wherein the addictive substance is a nicotine containing product such as tobacco, an opioids such as heroin, cocaine or morphine, a benzodiazepine or a benzodiazepin-like drug or alcohol.

* * * * *